US011878179B2

(12) United States Patent
Deininger et al.

(10) Patent No.: US 11,878,179 B2
(45) Date of Patent: Jan. 23, 2024

(54) MINIMALLY INVASIVE LEADLESS NEUROSTIMULATION DEVICE

(71) Applicant: Medtronic, Inc., Minneapolis, MN (US)

(72) Inventors: Steven Deininger, Plymouth, MN (US); Alan Shi, Plymouth, MN (US); Thomas M. Hillebrand, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 134 days.

(21) Appl. No.: 17/485,292

(22) Filed: Sep. 24, 2021

(65) Prior Publication Data

US 2022/0096845 A1 Mar. 31, 2022

Related U.S. Application Data

(60) Provisional application No. 63/198,053, filed on Sep. 25, 2020.

(51) Int. Cl.
*A61N 1/375* (2006.01)
*A61N 1/05* (2006.01)

(52) U.S. Cl.
CPC ......... *A61N 1/3756* (2013.01); *A61N 1/0551* (2013.01)

(58) Field of Classification Search
CPC ................ A61N 1/3756; A61N 1/0551; A61N 1/36007; A61N 1/375
See application file for complete search history.

(56) References Cited

U.S. PATENT DOCUMENTS 5,987,352 A 11/1999 Klein et al.
6,230,059 B1 5/2001 Duffin
(Continued)

FOREIGN PATENT DOCUMENTS

CN 104812438 A 7/2015
CN 105492069 A 4/2016
(Continued)

OTHER PUBLICATIONS

International Preliminary Report on Patentability from related PCT Application PCT/US2021/052094, dated Mar. 28, 2023, 7 pgs.
(Continued)

*Primary Examiner* — Mark W. Bockelman
(74) *Attorney, Agent, or Firm* — Patterson Thuente IP

(57) ABSTRACT

A leadless neurostimulation device including a header unit having at least one primary electrode having a contact surface that defines an external surface on a side of the device, an outer housing that forms a side of the header unit opposite of the contact surface of the primary electrode, and a dielectric mount that receives at least a portion of the primary electrode and at least partially surrounds the primary electrode, the dielectric mount being configured to electrically insulate the primary electrode from the outer housing, the dielectric mount being received and fixed within a recessed portion of the outer housing, and a housing having a secondary electrode positioned on the same side of the leadless neurostimulation device as the primary electrode, the primary electrode and the secondary electrode being configured to transmit an electrical stimulation signal therebetween to provide electrical stimulation therapy to a tibial nerve of a patient.

22 Claims, 6 Drawing Sheets

(56) References Cited

U.S. PATENT DOCUMENTS

| | | |
|---|---|---|
| 6,522,915 B1 | 2/2003 | Ceballos et al. |
| 6,735,474 B1 | 5/2004 | Loeb et al. |
| 7,894,907 B2 | 2/2011 | Cowan et al. |
| 9,220,911 B2 | 12/2015 | Gordon et al. |
| 9,351,648 B2 | 5/2016 | Mothilal et al. |
| 9,433,786 B2 | 9/2016 | Greiner et al. |
| 9,511,236 B2 | 12/2016 | Varady et al. |
| 9,555,246 B2 | 1/2017 | Jiang et al. |
| 9,597,518 B2 | 3/2017 | Deininger et al. |
| 10,238,880 B2 | 3/2019 | Thom et al. |
| 10,328,273 B2 | 6/2019 | Hovland et al. |
| 10,478,612 B2 | 11/2019 | Schepis et al. |
| 11,045,650 B2 | 6/2021 | Brink et al. |
| 2005/0288600 A1 | 12/2005 | Zhang et al. |
| 2007/0049975 A1* | 3/2007 | Cates ............... A61N 1/375 607/5 |
| 2008/0004535 A1 | 1/2008 | Smits |
| 2008/0119903 A1* | 5/2008 | Arcot-Krishnamurthy ............... A61N 1/365 607/17 |
| 2008/0195165 A1* | 8/2008 | Stahmann ............ A61B 5/0215 607/18 |
| 2008/0243200 A1 | 10/2008 | Scinicariello et al. |
| 2009/0082828 A1 | 3/2009 | Ostroff |
| 2012/0101326 A1 | 4/2012 | Simon et al. |
| 2012/0197337 A1 | 8/2012 | Su et al. |
| 2014/0163579 A1 | 6/2014 | Tischendorf et al. |
| 2017/0157405 A1 | 6/2017 | Deininger et al. |
| 2017/0224584 A1 | 8/2017 | Greiner et al. |
| 2017/0296426 A1 | 10/2017 | Oron et al. |
| 2019/0314635 A1 | 10/2019 | Iyer et al. |

FOREIGN PATENT DOCUMENTS

| | | |
|---|---|---|
| CN | 107106841 A | 8/2017 |
| CN | 109069825 A | 12/2018 |
| CN | 110062643 A | 7/2019 |
| CN | 111447969 A | 7/2020 |
| WO | WO 2014/153219 A1 | 9/2014 |

OTHER PUBLICATIONS

International Search Report and Written Opinion from PCT Application PCT/US2021/052094, dated Jan. 21, 2022, 9 pgs.

Application and file history for U.S. Appl. No. 29/652,586, filed Sep. 25, 2020, inventors Deininger et al.

Application and file history for U.S. Appl. No. 29/652,587, filed Sep. 25, 2020, inventors Deininger et al.

Application and file history for U.S. Appl. No. 17/485,303, filed Sep. 24, 2021, inventors Deininger et al.

Search report from related Chinese Application CN 202180070020.4, dated Jul. 26, 2023, 9 pgs. No english translation available.

Search report from related Chinese Application CN 202180071032.9, dated Aug. 9, 2023, 10 pgs. No english translation available.

* cited by examiner

MINIMALLY INVASIVE LEADLESS NEUROSTIMULATION DEVICE

CROSS-REFERENCE TO RELATED APPLICATIONS

This application claims the benefit of U.S. Provisional Application Ser. No. 63/198,053, filed Sep. 25, 2020, the disclosure of which is hereby incorporated by reference in its entirety. This application is related to, but does not claim the benefit of, U.S. Provisional Application Ser. No. 63/198,054 filed Sep. 25, 2020, and 63/199,274 filed Dec. 17, 2020, the disclosures of which are hereby incorporated by reference in their entireties.

TECHNICAL FIELD

The present application relates to implantable medical devices, and more specifically to minimally invasive implantable neurostimulation devices.

BACKGROUND

Implantable medical devices may be configured to deliver electrical stimulation therapy or monitor physiological signals. Electrical stimulation of nerve tissue, for example, may provide relief for a variety of disorders thereby improving the quality of life for many patients.

Some implantable medical devices (IMDs) may employ electrical leads that carry electrodes. For example, electrodes may be located at a distal portion of an elongate lead. Other examples of electrical leads may be relatively short, having one or more electrodes located along a body of the lead. Such electrical leads are provided separate from the housing or body of the IMD and coupled to the IMD during implantation to provide stimulation via the electrode at a location separated from the housing of the IMD.

Simulation of different nerve branches and clusters have been explored for treating various ailments. One avenue that has shown promising development has been the stimulation of the tibial nerve for the treatment of certain ailments such as incontinence or over-active bladder.

SUMMARY

Embodiments of the present disclosure are directed to minimally invasive, leadless neurostimulation devices. Leadless devices do not require the use of a separate lead and instead provide a unitary structured device that may be more robust and less invasive than lead-based counterpart devices.

The disclosed devices include a housing containing components therein configured for delivering neurostimulation therapy, and an attached header unit. The header unit includes one or more primary electrodes that form a portion of the exterior and side of the header unit. The one or more primary electrodes are electrically insulated from other portions of the exterior surface of the neurostimulation device. The housing of the neurostimulation device includes a secondary electrode that operates in conjunction with the one or more primary electrodes to provide electrical simulation therapy or neuro sensing capabilities. The secondary electrode is positioned on the same side of the device as the one or more primary electrodes positioned in the header unit.

In an embodiment, the disclosure describes system including a leadless neurostimulation device including a header unit having at least one primary electrode having a contact surface that defines an external surface on a side of the leadless neurostimulation device, an outer housing that forms a side of the header unit opposite of the contact surface of the primary electrode, and a dielectric mount that receives at least a portion of the at least one primary electrode and at least partially surrounds the at least one primary electrode, the dielectric mount being configured to electrically insulate the at least one primary electrode from the outer housing, the dielectric mount being received and fixed within a recessed portion of the outer housing, and a housing having a secondary electrode positioned on the same side of the leadless neurostimulation device as the at least one primary electrode, the at least one primary electrode and the secondary electrode being configured to transmit an electrical stimulation signal therebetween to provide electrical stimulation therapy to a tibial nerve of a patient.

In an embodiment, the disclosure describes a leadless neurostimulation device comprising a header unit comprising at least one primary electrode having a contact surface that defines an external surface on a side of the leadless neurostimulation device, an outer housing that forms a side of the header unit opposite of the contact surface of the primary electrode, and a dielectric mount that receives at least a portion of the at least one primary electrode and at least partially surrounds the at least one primary electrode, the dielectric mount being configured to electrically insulate the at least one primary electrode from the outer housing, the dielectric mount being received and fixed within a recessed portion of the outer housing, wherein the dielectric mount defines a channel between the outer housing and the dielectric mount, the channel configured to receive a medical adhesive therein to fix the outer housing to the dielectric mount, and wherein the primary electrode comprises an interior surface that defines an interlocking structure with the dielectric mount. The leadless neurostimulation device further includes a housing comprising a secondary electrode positioned on the same side of the leadless neurostimulation device as the at least one primary electrode, the at least one primary electrode and the secondary electrode being configured to transmit an electrical stimulation signal therebetween to provide electrical stimulation therapy to a tibial nerve of a patient, and a lead pin configured to pass through the mounting plate and connect to processing circuitry and components contained in the housing configured to transmit the electrical stimulation signal between the one or more primary electrodes or secondary electrodes to provide electrical stimulation therapy to the tibial nerve, wherein the primary electrode is electrically coupled to the lead pin. The leadless neurostimulation device further includes a mounting plate, wherein the housing is coupled to a first side of the mounting plate and the header unit is coupled to a second side of the mounting plate, and wherein the at least one primary electrode and the secondary electrode define a separation distance of about 10 mm to about 20 mm, and wherein the leadless neurostimulation device defines a total volume of about 1.5 cubic centimeters (cc) to about 3.5 cc.

In an embodiment, the disclosure describes a method of manufacturing a leadless neurostimulation device, the method comprising forming a header unit, including a primary electrode having a contact surface that defines an external surface on a side of the leadless neurostimulation device, forming the header unit comprising forming an outer housing as a side of the header unit opposite of the contact surface of the primary electrode, forming a dielectric mount to receive at least a portion of the primary electrode and at least partially surround the at least one primary electrode, the dielectric mount being configured to electrically insulate the at least one primary electrode from the outer housing, and fixing the dielectric mount within a recessed portion of the outer housing. The method of manufacturing further comprising forming a housing, including a secondary electrode positioned on the same side of the leadless neurostimulation device as the primary electrode.

The above summary is not intended to describe each illustrated embodiment or every implementation of the subject matter hereof. The figures and the detailed description that follow more particularly exemplify various embodiments.

BRIEF DESCRIPTION OF DRAWINGS

The disclosure can be more completely understood in consideration of the following detailed description of various embodiments of the disclosure, in connection with the accompanying drawings, in which.

Figure 1:
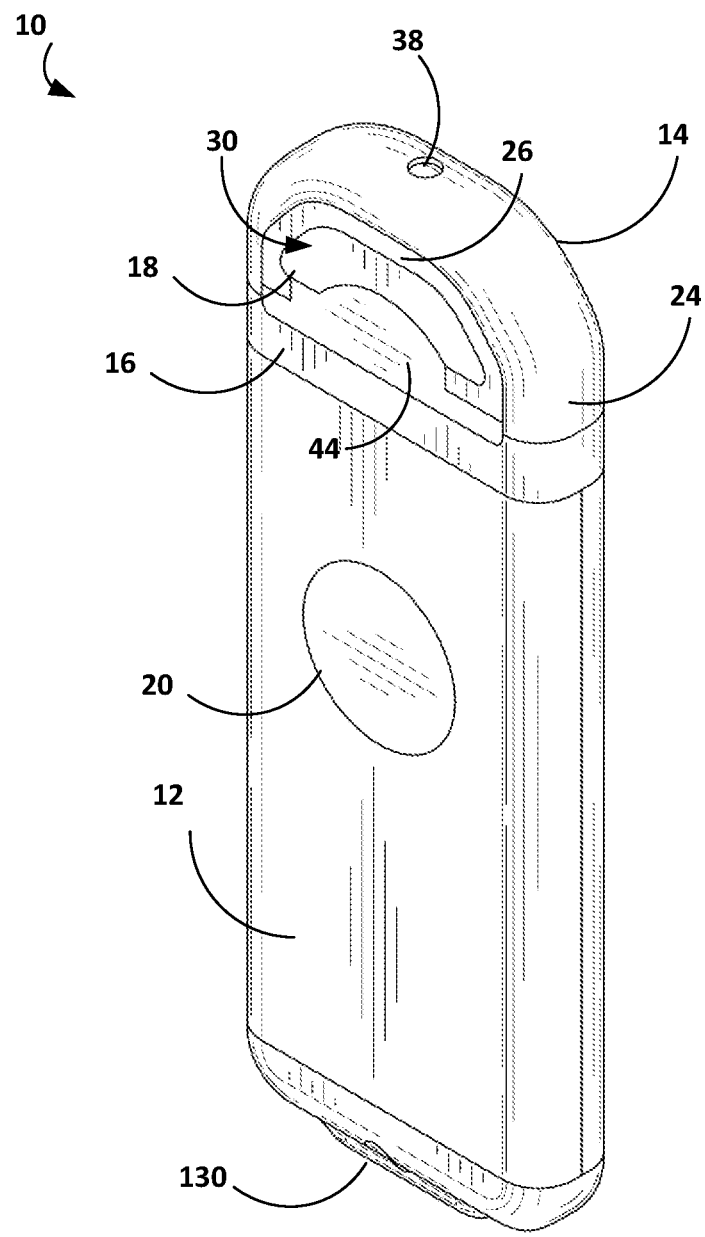
FIG. 1 is a schematic view showing an example leadless neurostimulation device as described herein.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Embodiments of leadless neurostimulation devices described herein may be useful for numerous types of neurostimulation therapies, such as for pain control, autonomic nervous system modulation, functional electrical stimulation, tremors, and more. In preferred embodiments, the leadless neurostimulation devices described herein may be useful for stimulating one or more nerves to control symptoms of overactive bladder, urgency frequency, nocturia, painful bladder syndrome, chronic pelvic pain, incontinence, or other pelvic health conditions. These embodiments may also be useful for stimulating one or more peripheral nerves to control pain in one or more areas of the body, such as a foot, ankle, leg, groin, shoulder, arm, wrist, or the back, for example. In one example, embodiments of the disclosed leadless neurostimulation devices may be used to stimulate a tibial nerve of a patient.

FIG. 1 is schematic view showing an example leadless neurostimulation device 10. Leadless neurostimulation device 10 includes a housing 12 containing components therein configured for delivering neurostimulation therapy, a header unit 14 that includes one or more primary electrodes 18, and a mounting plate 16 that couples housing 12 to header unit 14. Header unit 14 includes at least one primary electrode 18 that forms part of an exterior surface of header unit 14. Housing 12 includes a secondary electrode 20 that forms part of an exterior surface of housing 12 and is positioned on the same side of device 10 as primary electrode 18. In an alternate embodiment not depicted, primary electrode 18 and secondary electrode 20 may be arranged on opposite sides of device 10.

Primary electrode 18 and secondary electrode 20 operate in conjunction with one another to provide stimulation therapy to a target treatment site (e.g., a tibial nerve). Secondary electrode 20 may also be referred to as a case electrode, can electrode or reference electrode. In an embodiment, primary electrode 18 may comprise a cathode and secondary electrode 20 may comprise an anode. In some embodiments, primary and secondary electrodes 18 and 20 may be characterized as a bipolar pair or system.

The terms "primary" and "secondary" are used to differentiate two or more electrodes that are configured to transmit an electrical signal therebetween. The terms are not used to imply a hierarchy among the electrodes, positive and negative terminal, a total number of electrodes, or a directionality by which a signal is transmitted between the electrodes.

Figure 2A:
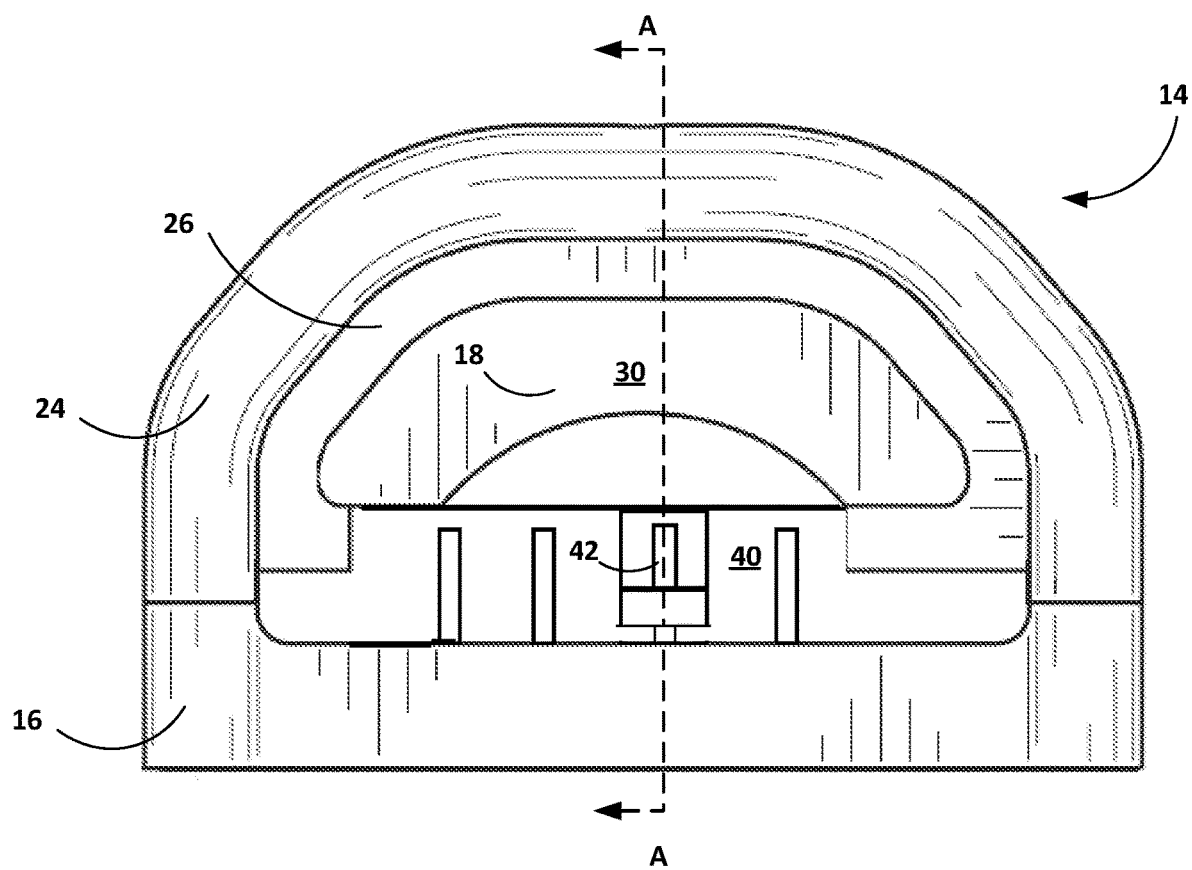
FIGS. 2A-2C are schematic views of an example header unit and mounting plate of the implantable leadless neurostimulation device of FIG. 1.
Figure 2B:
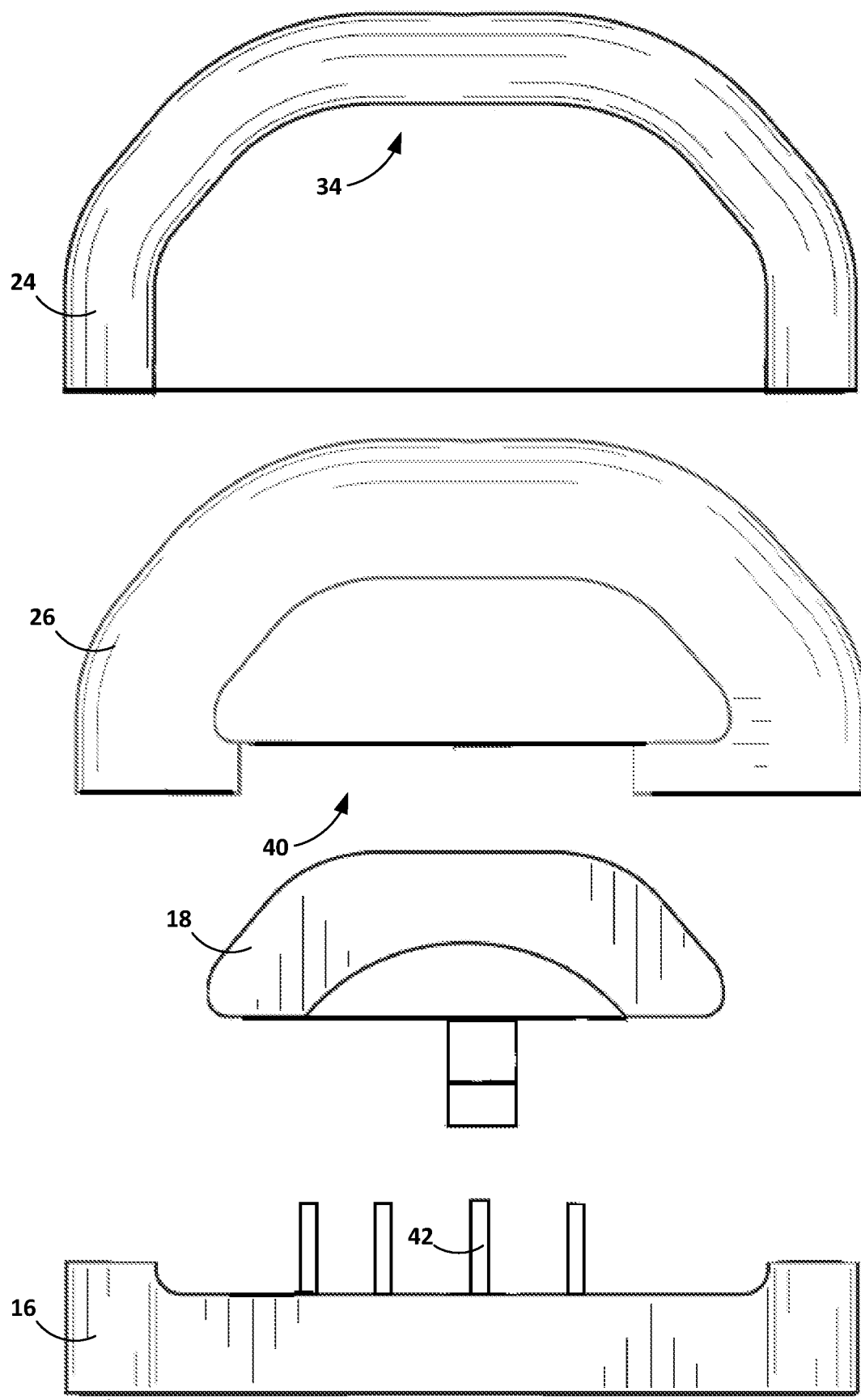
Figure 2C:
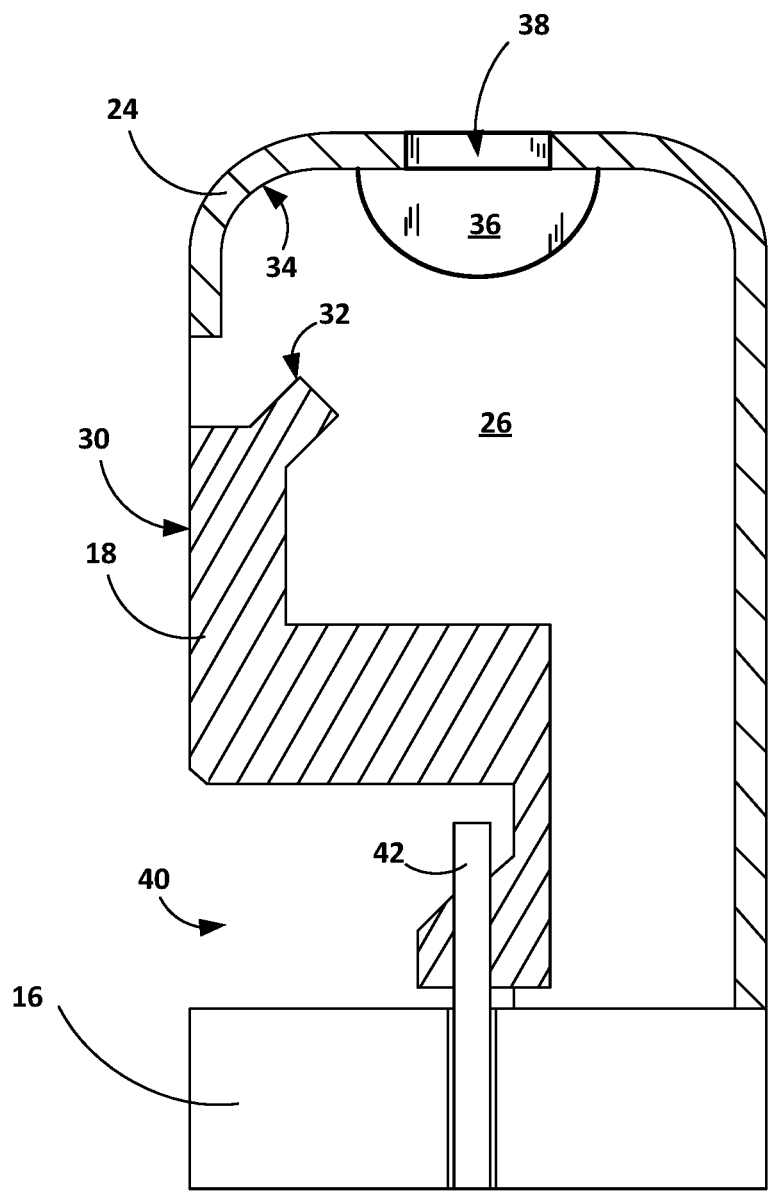

FIGS. 2A-2C provide various schematic views of mounting plate 16 and header unit 14 and the components contained therein. In particular, FIG. 2A is a schematic view of a partially assembled header unit 14 coupled to mounting plate 16. FIG. 2B is an exploded view that illustrates how the components of header unit 14 and mounting plate 16 are assembled. FIG. 2C is a cross sectional view of FIG. 2A along line A-A that illustrates portions of header unit 14.

Header unit 14 includes outer housing 24, primary electrode 18, and dielectric mount 26. Outer housing 24 is coupled to mounting plate 16 and may define a partially recessed cavity that receives dielectric mount 26 and primary electrode 18. Outer housing 24 and mounting plate 16 may be made of metal or metal alloy (e.g., titanium or titanium alloy) to allow for easy coupling there between (e.g., laser welding) as well as allow for the coupling of mounting plate 16 to housing 12. Additionally, or alternatively, outer housing 24 or mounting plate 16 may be composed of a ceramic material, or non-conductive plastic material (e.g., polypropylene) including appropriate mechanisms (e.g., metal inserts) for coupling outer housing 24 to mounting plate 16.

In some embodiments, the seam between mounting plate 16 and outer housing 26 may form at least a partial hermetic seal. As discussed further below, while portions of mounting plate 16 and outer housing 24 define the exterior shape and body of leadless neurostimulation device 10, the exterior surface of these components may be coated with a dielectric material to prevent the body of such components from interfering with the electrical pathway of primary electrode 18 and secondary electrode 20 as well as contribute to the hermetic seal of device 10. In an alternate embodiment not depicted, header unit 14 may be configured so as to be coupleable directly to housing 12, without the need for a separate mounting plate element.

Primary electrode 18 defines exterior contact surface 30 configured to be brought into direct contact with tissue of the patient. Contact surface 30 may also form a portion of a side of header unit 14, which is preferably on the same side of device 10 as secondary electrode 20. The exterior perimeter of contact surface 30 is bordered by dielectric mount 26, which also forms a portion of the exterior surface of header unit 14 and electrically insulates and physically separates primary electrode 18 from outer housing 24 and mounting plate 16.

Primary electrode 18 may be of any suitable size and shape to provide electrical stimulation to the tibial nerve through the fascia layer of a patient. In some embodiments, primary electrode 18 may define a contact surface area of about 15 mm² to about 90 mm². In preferred embodiments that include only a single primary electrode 18, the contact surface area may be greater than about 15 mm², greater than about 18 mm², greater than about 20 mm², less than 35 mm², less than 30 mm², and less than 25 mm². As discussed further in the provisional application Ser. Nos. 63/198,054 filed Sep. 25, 2020, and 63/199,274 filed Dec. 17, 2020, both entitled "MINIMALLY INVASIVE LEADLESS NEUROSTIMULATION DEVICE," incorporated by reference above, the surface area of primary and secondary electrodes 18 and 20, and separation distance there between may be optimized to provide sufficient penetration and stimulation of the tibial nerve through the fascia layer in a patient's leg.

In some embodiments, the size, shape, and physical separation distance between primary electrode 18 and secondary electrode 20 may be configured to produce an impedance of less than 2,000 ohms (e.g., between about 250 ohms and 1,000 ohms). Additionally, or alternatively, primary and secondary electrodes 18 and 20 may be arranged in a non-concentric arrangement such that one electrode does not substantially encircle the other.

In some embodiments, contact surface 30 of primary electrode may be substantially flat (e.g., flat or nearly flat) as shown in FIG. 1. Alternatively, primary electrode 18 may define a curved surface (e.g., a semi-cylindrical shape or other 2D or 3D curved plane) that helps primary electrode 18 follow the curvatures of the fascia layer of a patient when implanted to provide better contact and focusing of the electrical signal directed to the tibial nerve. The curved surface may extend over the entirety of contact surface 30, or only over a portion of the surface. Additionally, or alternatively, the curved curvature may be confined to only contact surface 30 of primary electrode 18, or may extend over other portions of device 10 such as other parts of header 14, mounting plate 16, or housing 12. By including the curvature over other portions of device 10, the device may provide a more ergonomic fit when implanted while also helping to direct the stimulation signal to the tibial nerve.

In some embodiments, contact surface 30 of primary electrode 18 may also protrude from the plane defined by housing 12. Such a protrusion may help apply additional pressure to the fascia of the patient and help guide the electrical stimulation signal deeper into the tissue of the patient. Primary electrode 18 may also define one or more interlocking features, carveouts, recesses, or other structures below contact surface 30 that reduce the overall volume of primary electrode 18 without interfering with contact surface 30. The reduced volume and interlocking features may also help reduce manufacturing costs as well as help fix primary electrode 18 relative to dielectric mount 26. In some embodiments, contact surface 30 may possess a textured finish such as a laser textured finish. The textured finish may be added to the general shapes described above. For example, contact surface 30 may be flat or curved with a laser texturing added to contact surface 30. In some examples, contact surface 30 may include a titanium, titanium alloy, or platinum iridium textured surface.

Primary electrode 18 may be formed using any suitable material capable of delivering electrical stimulation therapy to the patient once implanted and having desirable long-term biological compatibility with the surrounding tissue. Such materials may include, but are not limited to titanium, titanium alloy, platinum iridium, or the like. In preferred embodiments, at least contact surface 30 is formed of platinum iridium, titanium, titanium alloy, while the body of primary electrode 18 may be made of the same or different material. For example, the body of primary electrode 18 may be formed of titanium or titanium alloy with contact surface 30 formed of platinum iridium. Using platinum iridium may be beneficial in reducing or eliminating the potential for charge buildup on the external surface of device 10 during operation. Platinum iridium also provides low impedance with the surrounding bodily tissue, has great biological compatibility, and works well as a contact surface for implantable electrodes. However, platinum iridium can be costly or can have diminished compatibility (e.g., metallurgical bonding) with other metals or alloys.

In some embodiments, primary electrode 18 can be made entirely out of platinum iridium, titanium, or titanium alloy. Titanium or titanium alloy offers significant cost advantages over platinum iridium or other specialty metals. However, titanium-based electrodes have been generally discouraged in implantable devices that administer chronic or long-term stimulation therapy. It is believed that such titanium-based electrodes can develop an oxide surface layer with time. This oxide layer along the surface of the electrode can increase the impedance between the electrode and bodily tissue and lead to charge buildup along the outer surface. As a result, the efficacy of the stimulation therapy can diminish with time when using titanium-based electrodes requiring increased voltage or current to deliver therapeutic stimulation levels.

Due to the relatively large surface area of primary electrode 18 (e.g., approximately 21 mm²), the phenomenon of diminished efficacy while using a titanium-based electrode has been observed to be negligible or avoided altogether. Thus, titanium-based electrodes may be used for primary electrode 18 (including contact surface 30) without experiencing reduced efficacy in the stimulation therapy over the useful life of device 10. In some embodiments, primary electrode 18 can be made out of commercially pure titanium (e.g., metal comprised of >99% Ti, or Grade 2 titanium). Commercially pure titanium, particularly Grade 2 titanium, offers certain manufacturing advantages including, for example, the ability for primary electrode 18 to be produced through machine stamping rather than a casting or other costly fabrication process. Titanium and select titanium alloys also have general acceptance as being biologically compatible and suitable for construction of implantable medical devices.

Titanium and titanium alloys also offer good compatibility (e.g., metallurgical bonding) compared to platinum iridium with other metals and alloys. For example, lead pin 42, which is discussed further below, is used to couple primary electrode 18 to the device circuitry contained in housing 12. Lead pin 42 may be constructed of niobium or niobium alloy. Soldering or welding between niobium and platinum iridium has been found to have reduced metallurgical compatibility causing the introduction micro fractures and other indications of poor bonding through the well joint between the niobium and platinum iridium metals. These micro fractures can diminish the reliability and impedance of the device. In contrast, titanium has great compatibility with niobium and can be coupled to lead pin 42 efficiently through laser welding.

In some embodiments, improved bonding between niobium and platinum iridium through the use of an intermediary or constructing the body of primary electrode 18 using a different material than platinum iridium. For example, the body of primary electrode 18 can be made of titanium and surface 30 can be coated with platinum iridium (e.g. through sputtering or other deposition method) thereby offering the advantages of having contact surface 30 formed of platinum iridium while also obtaining good bonding capabilities through the use of titanium. Additionally, or alternatively, a titanium sleeve can be introduced between the niobium based lead pin 42 and platinum iridium body of primary electrode 18 to obtain a similar effect. The titanium improves the electrical coupling between lead pin 42 and primary electrode 18 because titanium can be efficiently welded or friction bonded to both niobium and platinum iridium. The titanium body or sleeve acts as an intermediary between the niobium and platinum iridium to eliminate the presence of micro fractures and other indications of poor bonding thereby improving the conductive transfer and reliability of device 10 over its lifespan.

Dielectric mount 26 is configured to conform to at least some of the internal surfaces of primary electrode 18 to help physically retain and electrically insulate primary electrode 18 from other portions of header unit 14 and mounting plate 16. In some embodiments, primary electrode 18 and dielectric mount 26 define interlocking interior surfaces 32 that allow primary electrode 18 to sit within dielectric mount 26 and help prevent physical separation (e.g., movement of primary electrode 18 out of device 10). For example, primary electrode 18 may define a retention channel, protuberance, or some other physical structure that forms at least a portion of a perimeter of the interior surface(s) of primary electrode and provides interlocking surface 32. Additionally, including the presence of a structure that provides interlocking surface 32 may help reduce the overall quantity of material used to form primary electrode 18 which may reduce manufacturing costs as well as help fix primary electrode 18 relative to dielectric mount 26 and header 14.

Dielectric mount 26 may be formed of any suitable material that electrically insulates primary electrode 18 from other portions of header unit 14 and mounting plate 16. In some embodiments, dielectric mount 26 may be formed of liquid silicone rubber (LSR), silicone, or similar material. For example, LSR, silicone, or other suitable dielectric material may be cast or molded around primary electrode 18 to produce a secure fit with primary electrode 18, prevent physical separation there between, and provide the desired physical and electrical separation from outer housing 26 and portions of mounting plate 16. In some embodiments, dielectric mount 26 may be formed integrally with outer housing 24 provided the components are formed of a non-conductive material.

In some embodiments, dielectric mount 26 may also include one or more recesses or strategically placed gaps, that may receive a medical adhesive to help aid with assembly of header unit 14. For example, as shown in FIGS. 2A-2C, dielectric mount 26 may be generally shaped to be received within the recessed area 34 defined by outer housing 24. Along a portion of the adjacent surfaces between dielectric mount 26 and outer housing 24, dielectric mount 26 may define a channel 36 configured to receive, after assembly, a suitable adhesive (e.g., non-conductive medical adhesive, epoxy volcanized silicone, or the like) that fixes dielectric mount 24 and outer housing 24 together. As best seen in FIGS. 1 and 2C, outer housing may define a filling port 38 that is in fluid communication with channel 36 and allows for injection of the adhesive after assembly.

Dielectric mount 26 may also be shaped to provide a gap 40 between mounting plate 16 and primary electrode 18. Upon assembly, gap 40 provides access for coupling the one or more primary electrodes 18 to the respective lead pins 42 which are used to electrically connect primary electrode 18 to the device circuitry contained in housing 12. After coupling primary electrode 18 to lead pin 42 (e.g., soldering), gap 40 may be filled with a dielectric material 44 such as the medical adhesive injected through fill port 38, LSR, silicone, or other suitable material.

Outer housing 24 may form the majority of the body of header unit 14. In particular, outer housing 24 forms the side of header unit 14 opposite of contact surface 30, the perimeter edges (apart from the contact surface provided with mounting plate 16), and a portion of the same side of header unit 14 as contact surface 30 of primary electrode 18. In some embodiments, outer housing 24 may have a rounded, semi-circular, or D-shaped perimeter edge that provides a relatively smooth surface without any abrupt or sharp edges or lines than may present an irritation to the patient after implantation. In some embodiments, outer housing 24 is configured to receive and form a partial shell around dielectric mount 26. As such, outer housing 24 may define a concave interior surface (not shown) that receives a portion of dielectric mount 26. Dielectric mount 26 may be secured to outer housing 26 using a suitable medical adhesive.

Header unit 14 is coupled to mounting plate 16 and likewise mounting plate 16 is coupled to housing 12. Housing 12 includes secondary electrode 20. In some embodiments, secondary electrode 20 may be defined by an area of the body of housing 12. For example, housing 12 may be formed of a metallic material (e.g., titanium) and electrically coupled to the processing circuitry of leadless neurostimulation device 10. The outer surface of housing 12, including portions of mounting plate 16 and header unit 14, may be coated with a dielectric material apart from the surface area that defines secondary electrode 20 and primary electrode 18. The dielectric material may at least partially encapsulate device 10 such that the boundary created by the dielectric material defines the area of secondary electrode 20, contact surface 30, or both.

The dielectric coating may be applied using any suitable technique. In some such examples, the areas defining contact surface 30 and secondary electrode 20 may be masked with a suitable material such as tape. Leadless neurostimulation device 10 may be then coated using vapor deposition, dip coating, spray coating of similar technique with an adherent dielectric material followed by subsequent removal of the mask material to expose the surfaces of contact surface 30 and secondary electrode 20.

Suitable dielectric materials for coating leadless neurostimulation device 10 may include, but are not limited to, parylene, LSR, or silicone. Additionally, or alternatively, the outer surface of neurostimulation device 10 or portions thereof, may include a surface treatment such as an anodization treatment to modify portions of the surface to make the surface non-conductive. For example, portions of housing 12, outer housing 24, or both, if made of metal (e.g., titanium) may be treated through anodization to make select surfaces non-electrically conductive. In such examples, for purposes of this disclosure the exterior surface of the components may still be characterized as being metal (e.g., titanium) although the component has received such surface treatment.

In preferred examples, the outer surface of leadless neurostimulation device 10 may be formed primarily of parylene. Formation of the desired electrode profiles may utilize dielectric blocking methods (e.g., use of a masking material during manufacture) or dielectric removal methods (e.g., removal via laser or soda blast) without damaging the dielectric coating.

In some embodiments, the dielectric coating may also contribute to creating a hermetic seal around leadless neurostimulation device 10. The general configuration of attaching header 14 and housing 12 respectively to mounting plate 16 may also produce a hermetic seal within device 10. Coating device 10 with a dielectric material possessing sealing properties such as parylene, LSR, or silicone may either provide additional robustness to the hermetic seal of device 10. Providing leadless neurostimulation device 10 in a hermetically sealed form may contribute to the device's long-term functionality thereby providing advantages over other non-hermetically sealed devices.

Secondary electrode 20 may define a contact surface area of about 40 mm$^2$ to about 120 mm$^2$. However, devices having larger sized secondary electrodes may increase the minimal current needed to create a therapeutic response. The separation distance between primary electrode 18 and secondary electrode 20 may be about 5 mm to about 15 mm.

The processing circuitry and components of neurostimulation device 10 are contained within housing 12. Examples of such processing components may include one or more electronic circuits for delivering electrical stimulation therapy, telemetry hardware, power supply, memory, processor(s). Housing 12 can also include communication circuitry disposed therein for receiving programming communication from an external programmer, or providing feedback to a programmer or other external device.

In one example, housing 12 can include an energy source enclosed therein, e.g., a rechargeable or non-rechargeable battery. In another example, leadless neurostimulator 10 can also be configured to receive energy signals from an external device and transduce the received energy signals into electrical power that is used to recharge a battery of the device, an energy source e.g., a battery, processing circuitry, and other necessary components enclosed therein. In some embodiments, device 10 can be configured to receive energy signals from an external device and transduce the received energy signals into electrical power that is used to recharge a battery of device 10. Additionally, or alternatively device 10 may include a non-rechargeable primary cell battery.

In some embodiments, housing 12 of leadless neurostimulation device 10, and its various processing components may be substantially similar to the housing portion of the InterStim Micro Neurostimulator available from Medtronic. The InterStim Micro Neurostimulator may be modified to receive header unit 14 described herein along with modifications to provide secondary electrode 20. The total volume of neurostimulation device 10 may be relatively small as well. In some embodiments device 10 may have a total volume of about 0.5 cubic centimeters (cc) to about 6 cc, about 1.5 cc to about 3.5 cc, or about 2 cc to about 3 cc.

Figure 3A:
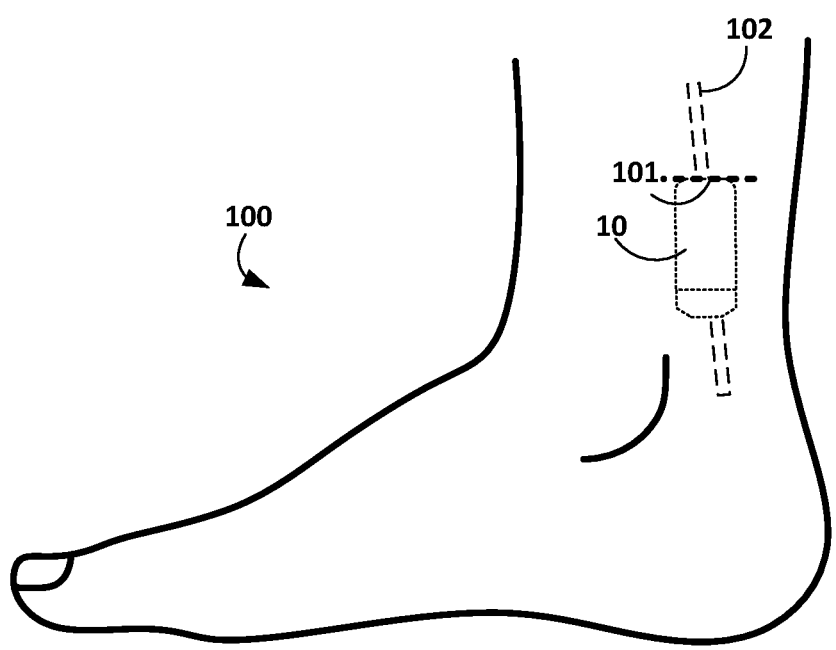
FIG. 3A is a side view of a patient's leg showing the leadless neurostimulation device of FIG. 1 implanted in the patient's leg near a tibial nerve.
Figure 3B:
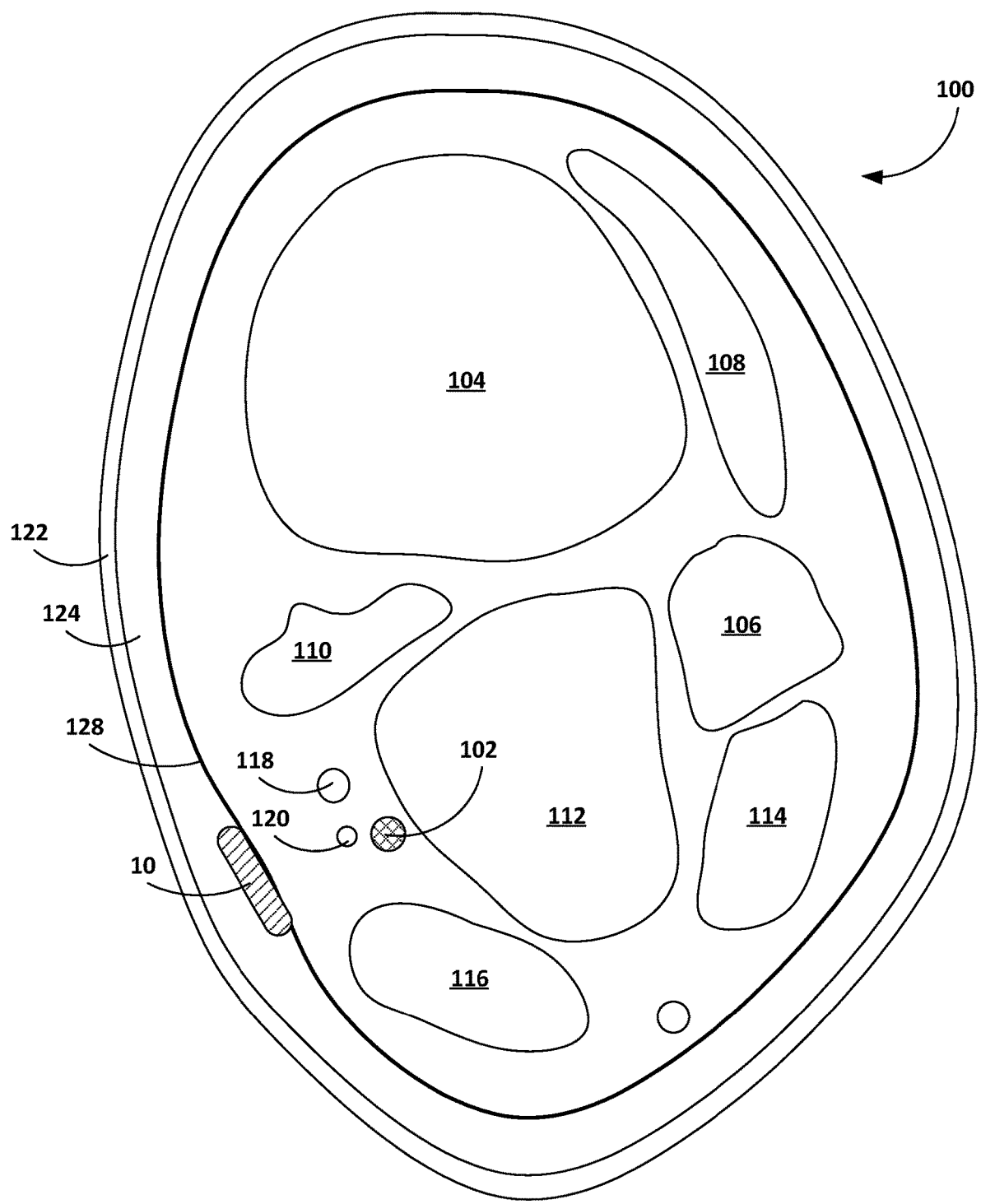
FIG. 3B is a cross-sectional view of a patient's leg showing the leadless neurostimulation device of FIG. 1 implanted near the patient's tibial nerve.

Referring now to implantation, FIG. 3A is a side view of a patient's leg 100 showing the leadless neurostimulation device 10 of FIG. 1 implanted and FIG. 3B shows a cross-sectional schematic view of leadless neurostimulation device 10 implanted in leg 100 of a patient near the ankle adjacent to the tibial nerve 102. The cross section of leg 100 illustrates tibia 104, fibula 106, fibularis tertius 108, flexor digitorum longus 110, flexor hallucis longus 112, fibularis brevis 114, soleus 116, posterior tibial artery 118, posterior tibial vein 120, skin 122, cutaneous fat layer 124, and fascia layer 126. Device 10 can be implanted through skin 122 and cutaneous fat layer 124 via a small incision 101 (e.g., about one to three cm) above the tibial nerve on a medial aspect of the patient's ankle. Device 10 may be positioned adjacent to the region defined by flexor digitorum longus 110, flexor hallucis longus 112, and soleus 116 in which tibial nerve 102 is contained and implanted adjacent and proximal to fascia layer 128 with primary electrode 18 and secondary electrode 20 facing toward tibial nerve 102.

In an embodiment, incision 101 does not cross fascia layer 128 thereby reducing the risk of complications with the surgical procedure. While incision 101 is shown approximately horizontal to the length of the tibial nerve, other incisions or implantation techniques could be used according to physician preference. In an embodiment, leadless neurostimulation device 10 may be implanted such that primary electrode 18 is oriented inferiorly relative to secondary electrode 20.

Optional testing of leadless neurostimulation device 10 may be performed to determine if device 10 is been properly positioned in proximity to tibial nerve 102 to elicit a desired response from an applied electrical stimulation. In an example, device 10 has controlled by an external programmer to deliver test stimulation, and one or more indicative responses are monitored, such as toe flexion from simulation of the tibial motor neurons controlling the flexor hallucis brevis or flexor digitorum brevis, or a tingling sensation in the heel or sole of the foot excluding the medial arch. If such testing does not elicit appropriate motor or sensory responses, the practitioner may reposition device 10 and retest.

Once a practitioner has determined device 10 is properly positioned to provide an appropriate patient response to delivered stimulation therapy, housing 12 can be secured in place if needed. Such anchoring means may be optional as the natural shape of the region in which device 10 is implanted, and the shape of device 10 itself has shown good compatibility with the surrounding tissue thus preventing device 10 from shifting or rolling after implantation, in some embodiments, leadless neurostimulation device 10 may further include one or more suture points to help secure device 10 to fascia 102 or other parts of leg 100. In some embodiments, a suture anchor 130 may be included at the distal end of housing 12, opposite of the end attached to mounting plate 16.

An advantage of the devices and methods described herein can be improved patient safety and satisfaction after implant. In contrast to other approaches, leadless neurostimulation device 10 does not require fascia layer 126 to be disturbed which may reduce risks affiliated with alternative procedures. Further, as device 10 is a unitary structure and can be hermetically sealed, the device is more robust than other lead-based stimulation units.

During operation, an electrical stimulation signal may be transmitted between primary electrode 18 and secondary electrode 20 through facia layer 126. The electrical signal may be used to stimulate tibial nerve 102 which may be useful in the treatment of overactive bladder (OAB) symptoms of urinary urgency, urinary frequency and/or urge incontinence, or fecal incontinence.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer). Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

What is claimed is:

1. A leadless neurostimulation device comprising:
   a header unit comprising:
      at least one primary electrode having a contact surface that defines an external surface on a side of the leadless neurostimulation device;
      an outer housing that forms a side of the header unit opposite of the contact surface of the primary electrode; and
      a dielectric mount that receives at least a portion of the at least one primary electrode and at least partially surrounds the at least one primary electrode, the dielectric mount being configured to electrically insulate the at least one primary electrode from the outer housing, the dielectric mount being received and fixed within a recessed portion of the outer housing; and
   a housing comprising a secondary electrode positioned on the same side of the leadless neurostimulation device as the at least one primary electrode, the at least one primary electrode and the secondary electrode being configured to transmit an electrical stimulation signal therebetween to provide electrical stimulation therapy to a tibial nerve of a patient.

2. The leadless neurostimulation device of claim 1, wherein the primary electrode comprises an interior surface that defines an interlocking structure with the dielectric mount.

3. The leadless neurostimulation device of claim 1, further comprising a lead pin configured to pass through a mounting plate and connect to processing circuitry and components contained in the housing configured to transmit the electrical stimulation signal between the one or more primary electrodes or secondary electrodes to provide electrical stimulation therapy to the tibial nerve, wherein the primary electrode is electrically coupled to the lead pin.

4. The leadless neurostimulation device of claim 3, wherein the one or more primary electrodes may comprise Grade 2 titanium, a titanium alloy, or a Platinum-Iridium alloy, and wherein the lead pin comprises niobium.

5. The leadless neurostimulation device of claim 1, wherein the dielectric mount defines a channel between the outer housing and the dielectric mount, the channel configured to receive a medical adhesive deposited therein to fix the outer housing to the dielectric mount.

6. The leadless neurostimulation device of claim 5, wherein the outer housing defines a filling port in fluid communication with the channel to allow injection of the medical adhesive into the channel.

7. The leadless neurostimulation device of claim 1, wherein the contact surface of the at least one primary electrode is about 15 $mm^2$ to about 35 $mm^2$.

8. The leadless neurostimulation device of claim 1, wherein the contact surface of the at least one primary electrode is about 20 $mm^2$ to about 25 $mm^2$.

9. The leadless neurostimulation device of claim 1, wherein the at least one primary electrode and the secondary electrode define a separation distance of about 10 mm to about 20 mm.

10. The leadless neurostimulation device of claim 1, wherein the secondary electrode defines a contact surface area of about 40 $mm^2$ to about 120 $mm^2$.

11. The leadless neurostimulation device of claim 1, further comprising a dielectric coating that at least partially encapsulates the leadless neurostimulation device.

12. The leadless neurostimulation device claim 11, wherein a boundary defined by the dielectric coating defines the secondary electrode.

13. The leadless neurostimulation device of claim 1, wherein the device defines a total volume of about 1.5 cubic centimeters (cc) to about 3.5 cc.

14. The leadless neurostimulation device of claim 1, further comprising a mounting plate, wherein the housing is coupled to a first side of the mounting plate and the header unit is coupled to a second side of the mounting plate.

15. A leadless neurostimulation device comprising:
   a header unit comprising:
      at least one primary electrode having a contact surface that defines an external surface on a side of the leadless neurostimulation device;

an outer housing that forms a side of the header unit opposite of the contact surface of the primary electrode; and a dielectric mount that receives at least a portion of the at least one primary electrode and at least partially surrounds the at least one primary electrode, the dielectric mount being configured to electrically insulate the at least one primary electrode from the outer housing, the dielectric mount being received and fixed within a recessed portion of the outer housing, wherein the dielectric mount defines a channel between the outer housing and the dielectric mount, the channel configured to receive a medical adhesive therein to fix the outer housing to the dielectric mount, wherein the primary electrode comprises an interior surface that defines an interlocking structure with the dielectric mount;

a housing comprising a secondary electrode positioned on the same side of the leadless neurostimulation device as the at least one primary electrode, the at least one primary electrode and the secondary electrode being configured to transmit an electrical stimulation signal therebetween to provide electrical stimulation therapy to a tibial nerve of a patient;

at least one lead pin configured to pass through a mounting plate and connect to processing circuitry and components contained in the housing configured to transmit the electrical stimulation signal between the one or more primary electrodes or secondary electrodes to provide electrical stimulation therapy to the tibial nerve, wherein the primary electrode is electrically coupled to the lead pin; and a mounting plate, wherein the housing is coupled to a first side of the mounting plate and the header unit is coupled to a second side of the mounting plate, wherein the at least one primary electrode and the secondary electrode define a separation distance of about 10 mm to about 20 mm, and wherein the leadless neurostimulation device defines a total volume of about 1.5 cubic centimeters (cc) to about 3.5 cc.

16. A method of manufacturing a leadless neurostimulation device, the method comprising:

forming a header unit, including a primary electrode having a contact surface that defines an external surface on a side of the leadless neurostimulation device, forming the header unit comprising:

forming an outer housing as a side of the header unit opposite of the contact surface of the primary electrode;

forming a dielectric mount to receive at least a portion of the primary electrode and at least partially surround the at least one primary electrode, the dielectric mount being configured to electrically insulate the at least one primary electrode from the outer housing; and fixing the dielectric mount within a recessed portion of the outer housing; and forming a housing, including a secondary electrode positioned on the same side of the leadless neurostimulation device as the primary electrode.

17. The method of manufacturing of claim 16, wherein the step of forming a header unit further comprises forming the primary electrode with an interior surface that defines an interlocking structure with the dielectric mount.

18. The method of manufacturing of claim 17, further comprising:

coating at least a portion of the leadless neurostimulation device with a dielectric material; and defining the secondary electrode with a boundary of the dielectric material.

19. The method of manufacturing of claim 16, further comprising:

forming the at least one lead pin, passing the lead pin through a mounting plate, connecting the lead pin to processing circuitry and components contained in the housing configured to transmit the electrical stimulation signal between the one or more primary electrodes or secondary electrodes, and electrically coupling the lead pin to the primary electrode.

20. The method of manufacturing of claim 19, wherein electrically coupling the lead pin to the primary electrode comprises:

coupling the primary electrode directly to the lead pin, wherein the primary electrode comprises titanium or platinum iridium; or coupling a titanium sleeve to the lead pin as an intermediary between the lead pin and the primary electrode.

21. The method of manufacturing of claim 16, wherein the dielectric mount defines a channel between the outer housing and the dielectric mount, the method further comprising:

depositing a medical adhesive in the channel so as to fix the outer housing to the dielectric mount.

22. The method of manufacturing of claim 16, wherein the outer housing defines a filling port in fluid communication with the channel, the step of depositing the medical adhesive in the channel further comprising:

injecting medical adhesive into the filling port.

* * * * *